United States Patent
Danylyk

(10) Patent No.: US 6,673,217 B2
(45) Date of Patent: Jan. 6, 2004

(54) E-WATER MACHINE

(76) Inventor: Donald Bohdan Danylyk, 1538 Ohio Ave., Virginia Beach, VA (US) 23454

( * ) Notice: Subject to any disclaimer, the term of this patent is extended or adjusted under 35 U.S.C. 154(b) by 145 days.

(21) Appl. No.: 10/054,176

(22) Filed: Jan. 22, 2002

(65) Prior Publication Data

US 2003/0137304 A1 Jul. 24, 2003

(51) Int. Cl.$^7$ .................. C25D 17/00; B03C 1/02
(52) U.S. Cl. ...................... 204/212; 210/223
(58) Field of Search .................. 204/212, 119, 204/296, 117, 128, 195 R, 230, 129, 272, 275; 210/223, 268, 359, 926, 363; 205/566, 721, 701

(56) References Cited

U.S. PATENT DOCUMENTS

| | | | | |
|---|---|---|---|---|
| 3,725,236 A | * | 4/1973 | Johnson, Jr. | 204/408 |
| 3,829,366 A | * | 8/1974 | Ives et al. | 205/566 |
| 4,171,250 A | * | 10/1979 | Eddleman | 205/608 |
| 5,198,083 A | * | 3/1993 | Thornton | 205/688 |
| 5,711,874 A | * | 1/1998 | Kawata | 210/223 |
| 5,788,820 A | * | 8/1998 | Liu | 204/212 |

* cited by examiner

Primary Examiner—Rajnikant B. Patel

(57) ABSTRACT

The Present invention relates generally to the small cluster water field. The present invention relates to water and a processing method thereof to produce water having small clusters, and superior quality to other small cluster waters. This invention relates to a new and novel way of producing high quality physiologically active small cluster water.

9 Claims, 1 Drawing Sheet

E-WATER MACHINE

FIELD OF THE INVENTION

The present invention relates to water and a processing method thereof to produce water having small clusters, and superior quality to other small cluster waters.

BACKGROUND OF THE INVENTION

Water forms clusters (groups of molecules) consisting of a large number of ($H_2O$) molecules. The molecules are held in clusters by hydrogen bonds and vary in size. Water whose clusters are small are useful physiologically as follows: it tastes good due to effects on taste buds; it gets absorbed into cells easily to activate them; and it accelerates the absorption of food because of rapid absorption through the digestive tract; and has many other health benefits. Many people could greatly benefit from drinking high quality small cluster water, especially older people.

Well-known means for producing such small cluster water are by breaking hydrogen bonds by supersonics waves, infrared rays acting on water, magnetic fields acting on water and electric fields acting on water.

The object of the present invention is to produce a high-quality small cluster water machine. The present invention uses a variable voltage method to produce superior small cluster water in physiological effect.

DISCLOSURE OF THE INVENTION

The present inventor investigated the above disclosed invention and found high-quality small cluster water could be produced at voltages from 8 volts to 70 volts with an optimum mineral content in the water of 25 PPM (Parts Per Million) to 35 PPM. Water below 25 PPM did not produce high-quality small cluster water at these voltages. It was also found that a decreasing variable voltage when applied to the water produced high-quality small cluster water in less than one minute on the negative electrode side. The decreasing variable voltage is important in producing high quality small cluster water.

In one embodiment of the invention, the initial voltage of 18 volts was gradually decreased to zero volts over a period of one minute. The invention also worked successfully up to about 70 volts of initial voltage. Higher voltages did not produce high quality small cluster water. Accordingly, the present inventor developed the invention containing the required electric requirements and in a simple form. The invention consists of two ordinary household cups made of plastic, glass or ceramic. Both cups are filled to the brim with mineral water. Placing a water wicking material between the water in both cups forms a water bridge. The water bridge is used to make an electric conductive path between the two cups. The water wicking material could be a cotton ball, a wet able fabric, fiberglass wicking material or any wet able material. A conductive electrode from the invention is placed into each cup. The invention produces the required voltage on the two electrodes for the proper time. The person drinks only the water in the cup where the negative electrode was placed. The water in the cup, where the positive electrode was placed, is thrown away and not drunk.

BEST MODE TO CARRYING OUT THE INVENTION

Figure 1:
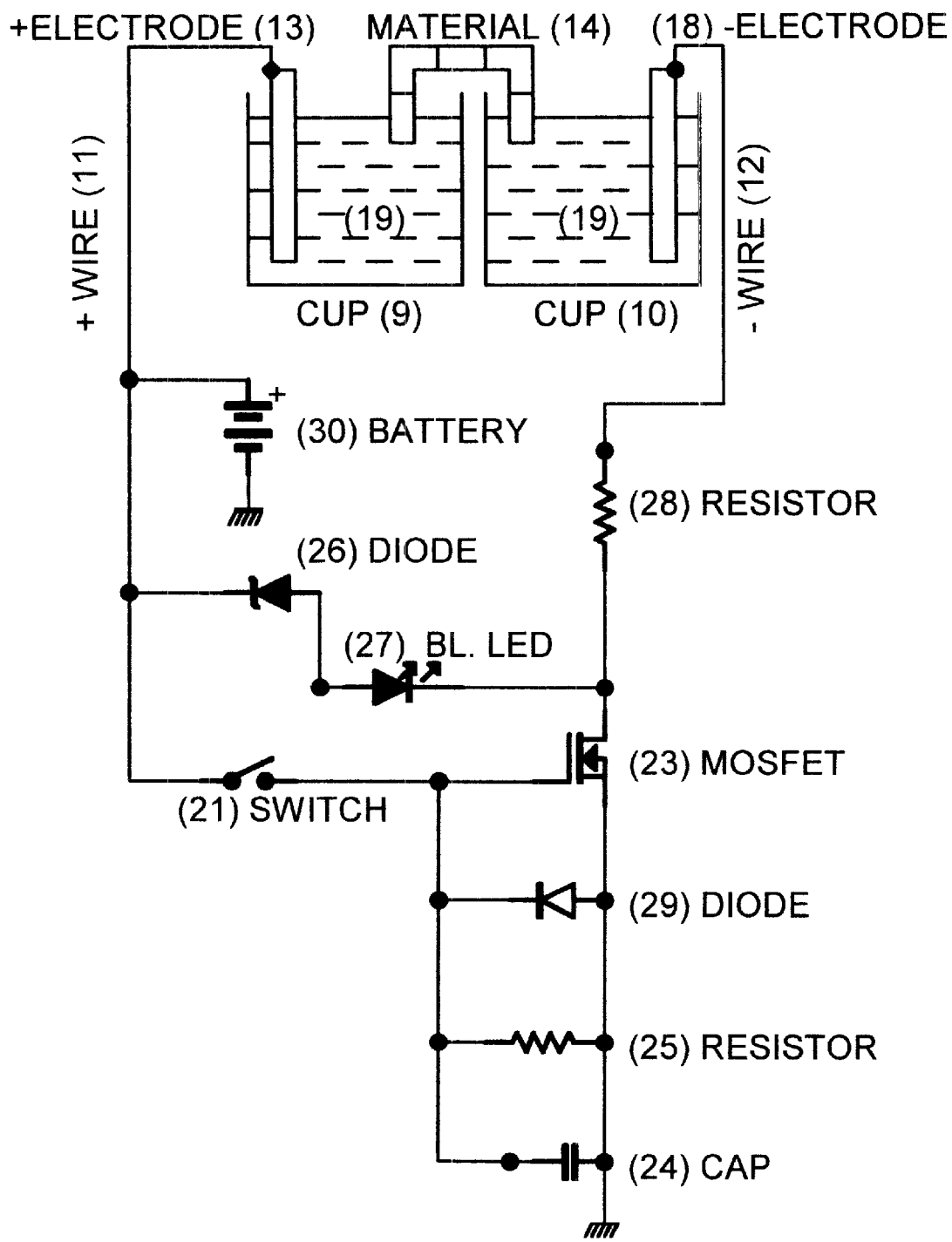
FIG. 1 is a schematic drawing of the present invention showing the two cups, and a water wicking material connecting both cups, and an electrode in each cup with a wire going to the invention. This apparatus is connected to an electronic circuit to produce the proper voltage and timing according to the invention.

Referring now to FIG. 1, the water treating invention consists of an electronic circuit and batteries. A positive wire (11) and a negative wire (12) are used to carry the voltage to the positive conductive electrode (13) and negative conductive electrode (18), which are immersed in the mineral water (19) in each of the cups (9) (10). The conductive electrodes could be stainless steel, carbon or other suitable electrically conductive material. The two plastic cups filled with mineral water are connected by water-wicking material (14), which has soaked up the mineral water.

One way to prepare mineral water of about 25 PPM is as follows: A mineral concentrate is prepared by adding one teaspoon of ordinary baking soda to eight ounces of water. One teaspoon of the mineral concentrate is added to one gallon of distilled or reverse osmosis water to produce about 25 PPM mineral water for use with the invention. Any other soluble mineral substance could be used in place of the baking soda. The mineral content in the optimum mineral range did not drain excessive current from the batteries than their typical use. Higher concentrations of water can be used with the invention as long as the mineral concentration in the water in the positive electrode cup is greater than or equal to the mineral concentration in the negative electrode cup.

Referring now to FIG. 1, the electronic circuit of the invention will be described. When push button momentary switch (21) is on, the voltage builds up to 18 volts on the gate (22) of the MOSFET transistor (23) and also charges the capacitor (24). When the push button is released, the capacitor discharges slowly through resistor (25) and the MOSFET (23) increases in resistance as the voltage drops on capacitor (24), therefore the voltage across the two electrodes decreases over time. Therefore the MOSFET transistor acts as a variable resistance, which changes the voltage to the two electrodes for the proper amount of time. Any type of variable resistance could be substituted for the MOSFET (23). By adjusting the value of the capacitor (24) and resistor (25), the time that the MOSFET (23) functions can be changed.

The 12-volt zener diode (26) and blinking LED (27) indicate that the circuit is on, and also indicate when the battery voltage goes below 13 volts to indicate the need to replace the two 9 volt batteries (30). The blinking LED (27) will not blink, when batteries (30) go below 13 volts, when the switch (21) is pressed.

The diode (29) provides protection to the MOSFET and is a good design practice. The resistor (28) also protects the MOSFET, by limiting current through the MOSFET in case the electrodes accidentally touched each other when the MOSFET is on.

This simple low-cost electronic circuit provides the necessary features for the invention.

The invention is, of course, not limited to the specific embodiments described and illustrated but may be realized in various modifications, substitutions, adaptations or combinations without departing from the spirit and scope of the appended claims.

I claim:

1. An apparatus for producing high quality small cluster water for affecting living beings, comprising:

a means for producing an initial voltage of 8 volts to 70 volts;

a means for producing a decreasing variable voltage that gradually lowers toward zero volts over a time period of greater than 15 seconds;

a means for conducting the said voltage to two electrodes;

a pair of cups holding mineralized water into which a said electrode is placed in each cup;

a water-wicking material, wet with mineralized water, connecting said one cup with the other cup.

2. The apparatus of claim 1, wherein the said water wicking material is a cotton ball, a wet able fabric or fiberglass wicking.

3. The apparatus of claim 1, wherein the said electrodes are made from stainless steel, carbon or other electrically conductive material.

4. The apparatus of claim 1, wherein the said decreasing variable voltage is produced by an electronic circuit or variable resistance.

5. The apparatus of claim 1, wherein the said initial voltage is produced by batteries.

6. An electronic circuit for indicating a good battery condition in a small cluster water apparatus of claim 1 consisting of a zener diode, blinking LED, and MOSFET connected in series across the battery terminal; and a switch connected to the gate of the MOSFET going to the positive terminal of the battery. In addition, the MOSFET may have another function to also control voltages to the apparatus.

7. The circuit of claim 6, wherein the said blinking LED blinks when the battery is good and does not blink when the battery is bad.

8. The circuit of claim 6, wherein the said zener diode can determine by its value at what voltage the battery condition will indicate bad.

9. The circuit of claim 6, wherein the said a resistor and capacitor are connected in parallel, from the gate of the MOSFET to the battery negative terminal, to provide a timing control to the MOSFET.

* * * * *